United States Patent [19]

VandenBerg

[11] Patent Number: Plant 7,009

[45] Date of Patent: Aug. 29, 1989

[54] CHRYSANTHEMUM PLANT NAMED TANAGA

[75] Inventor: Cornelis P. VandenBerg, Salinas, Calif.

[73] Assignee: Yoder Brothers, Inc., Barberton, Ohio

[21] Appl. No.: 247,526

[22] Filed: Sep. 22, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Tanaga particularly characterized by its flat capitulum form; quilled daisy capitulum type; bronze ray floret color; diameter across face of capitulum of up to 7 cm at maturity; medium plant height with spreading and prolific branching pattern; average natural season flower date of September 1 in Salinas, Calif. and September 28 in Hightstown, N.J.; uniform seven week photoperiodic flowering response to short days in photoperiodic controlled flowering programs; and durable, uniform performance in outside fall flowerings and in spring small pot flowering programs.

3 Drawing Sheets

The present invention comprises a new and distinct cultivar of Chrysanthemum, botanically known as *Dendranthema grandiflora,* and referred to by the cultivar name Tanaga.

Tanaga, identified as 85-047001, was originated from a cross made by the inventor, Cornelis P. VandenBerg, in a controlled breeding program in Salinas, Calif., in 1985.

The female parent and the male parent of Tanaga were both unnamed seedlings, identified as 79-M56002 and 82-M29001 respectively.

Tanaga was discovered and selected as one flowering plant within the progeny of the stated cross by Cornelis P. VandenBerg in January 1986, in a controlled environment in Salinas, Calif.

The first act of asexual reproduction of Tanaga was accomplished when vegetative cuttings were taken from the initial selection in April 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Tanaga are firmly fixed and are retained through successive generations of asexual reproduction.

Tanaga has not been observed under all possible environmental conditions. The phenotype may vary significantly with variations in environment such as temperature, light intensity and daylength.

The following observations, measurements and comparisons describe plants grown in a controlled open area in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Tanaga, which, in combination, distinguish this Chrysanthemum as a new and distinct cultivar:

1. Flat capitulum form.
2. Quilled daisy capitulum type.

3. Bronze ray floret color.
4. Diameter across face of capitulum up to 7 cm at maturity.
5. Medium plant height.
6. Spreading and prolific branching pattern.
7. Average natural season flower date of September 1 in Salinas, Calif., and September 28 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Tanaga, with the colors being as nearly true as possible with illustrations of this type. Sheet 1 is a color photograph of Tanaga grown as a pinched spray pot mum. Sheet 2 is a black and white photograph of three views of the inflorescence of Tanaga. Sheet 3 is a black and white photograph showing the upper and under sides of the leaves of Tanaga at three stages of development (mature, intermediate and immature).

The combination of capitulum type and ray floret color is not represented in any commercial garden mum cultivar known to the inventor. Capitulum type most similar in comparison to Tanaga is Illusion, disclosed in the inventor's plant patent application, Ser. No. 099,741. Reference is made to attached Chart A, which compares certain characteristics of Tanaga to the same characteristics of Illusion.

Similar traits are branching pattern and controlled response. Tanaga is bronze, with a quilled capitulum type, while Illusion is white, with a slight spoon-tipped ray floret. Tanaga has a smaller diameter of capitulum, a taller plant height and a slightly later natural season flower date than Illusion.

In the following description color references are made to The Royal Horticultural Society Colour Chart. The exact floret color of Tanaga is not represented in The R.H.S. Colour Chart, and the color values given are those closest to the actual color of Tanaga. The color values were determined May 20, 1988 on plant material grown in a controlled greenhouse environment in Salinas, Calif.

CLASSIFICATION

Botanical: *Dendranthema grandiflora.* cv. Tanaga.
Commercial: Quilled daisy spray pot mum and garden mum.

INFLORESCENCE

A. Capitulum:
*Form.*—Flat.
*Type.*—Quilled daisy.
*Diameter across face.*—Up to 7 cm at maturity.

B. Corolla of ray florets:
*Color (general tonality from a distance of three meters).*—Bronze.
*Color (upper surface).*—Base color 11A, tinged with 178D.
*Color (under surface).*—Base color 11A, more tinged and streaked with 178D than upper surface. Tinging with 178D is most pronounced in mature buds just prior to opening.
*Shape.*—Tubular, straight.

C. Corolla of disc florets:
*Color (mature).*—14A to 14B.
*Color (immature).*—Closest to 154A to 154B.

D. Reproductive organs:
*Androecium.*—Present on disc florets only; moderate pollen.
*Gynoecium.*—Present on both ray and disc florets.

PLANT

A. General appearance:
*Height.*—Medium.
*Branching pattern.*—Spreading and prolific.

B. Foliage:
*Color (upper surface).*—137A.
*Color (under surface).*—137B.
*Shape.*—Small, lobed.

CHART A

COMPARISON OF TANAGA AND ILLUSION

| Cultivar | Tanaga | Illusion |
|---|---|---|
| Ray Floret Color | Bronze | White |
| Capitulum Form and Type | Quilled Daisy | Spooned Daisy |
| Branching Pattern | Spreading and Prolific | Spreading and Prolific |
| Diameter Across Face of Capitulum | Up to 7 cm | Up to 8.5 cm |
| Plant Height | Medium | Short |
| Controlled Response | 7 Weeks | 7 Weeks |
| Average Natural Season Flowerdate: | | |
| In Salinas, CA | September 1 | August 29 |
| In Hightstown, NJ | September 28 | September 25 |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

I claim:

1. A new and distinct Chrysanthemum plant named Tanaga, as described and illustrated.

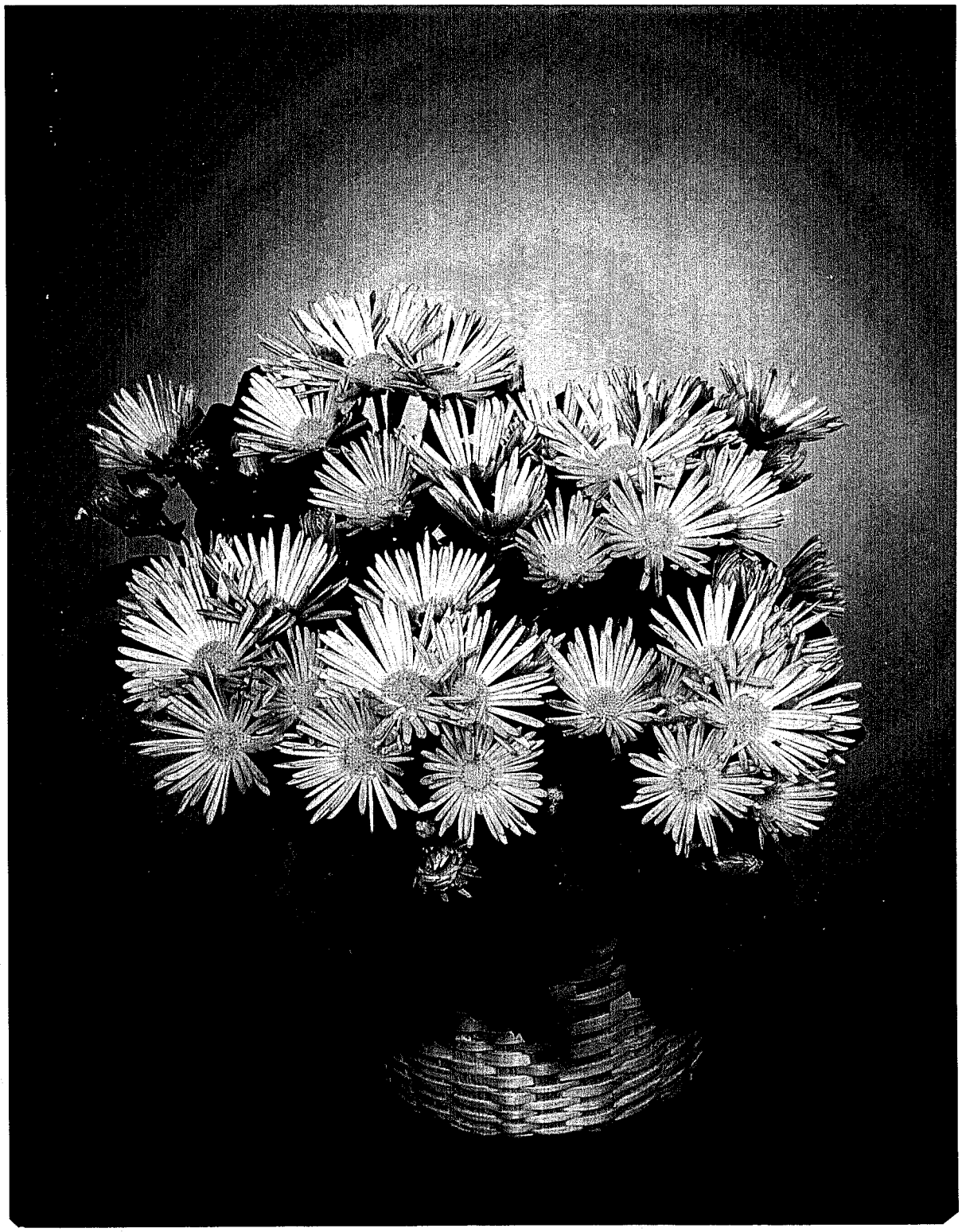

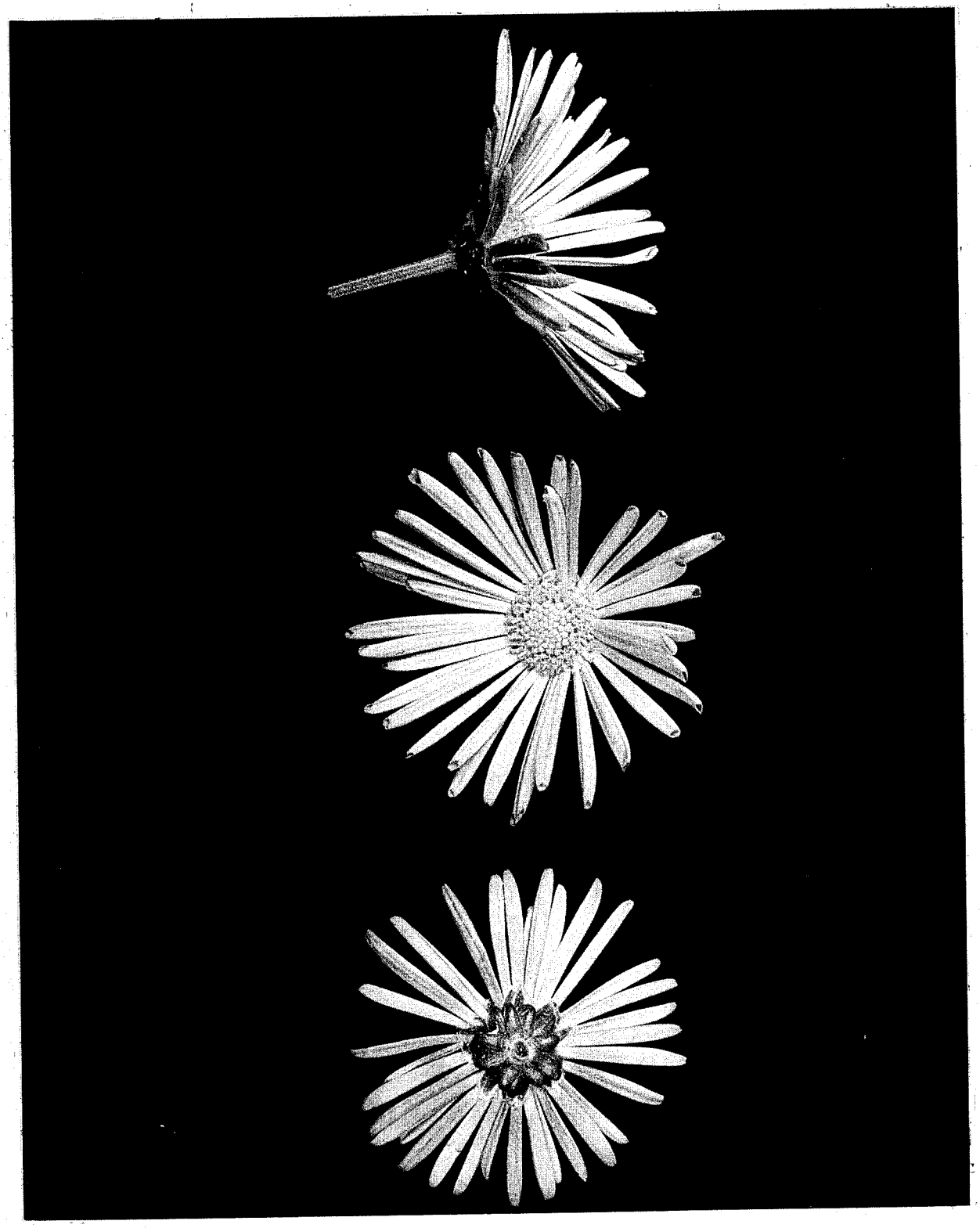

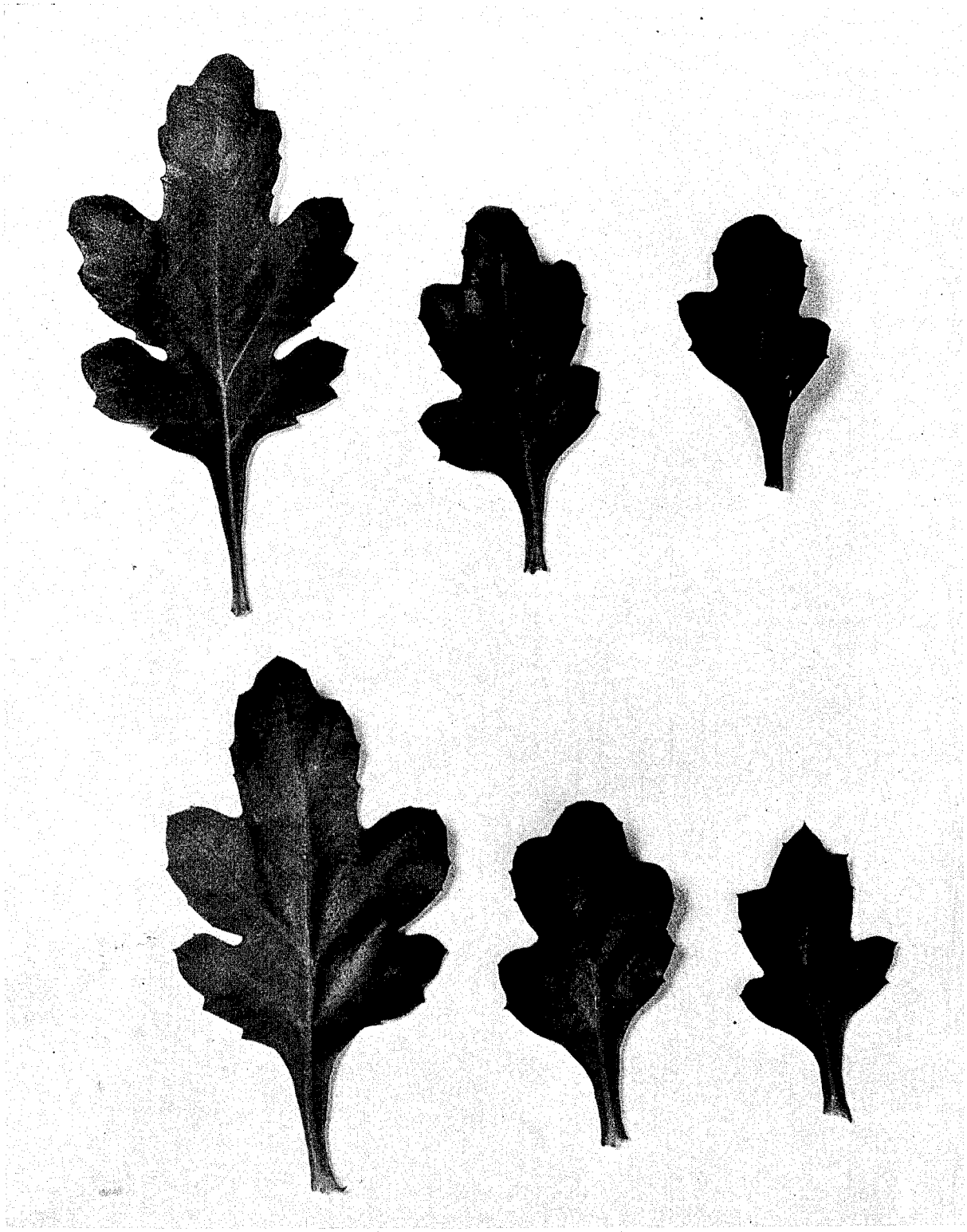

* * * * *